United States Patent
Yamazaki et al.

(10) Patent No.: US 7,943,027 B2
(45) Date of Patent: May 17, 2011

(54) ELECTROPHORESIS UNIT AND ELECTROPHORETIC ANALYSIS METHOD

(75) Inventors: Motohiro Yamazaki, Mito (JP); Ryoji Inaba, Hitachinaka (JP); Satoshi Takahashi, Hitachinaka (JP); Tomohiro Shoji, Hitachinaka (JP); Takeshi Ohura, Hitachinaka (JP); Takashi Gomi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 709 days.

(21) Appl. No.: 11/979,570

(22) Filed: Nov. 6, 2007

(65) Prior Publication Data

US 2008/0110756 A1 May 15, 2008

(30) Foreign Application Priority Data

Nov. 10, 2006 (JP) .................. 2006-304686

(51) Int. Cl.
*G01N 27/447* (2006.01)
*G01N 27/453* (2006.01)

(52) U.S. Cl. ......... 204/461; 204/452; 204/603; 204/612
(58) Field of Classification Search .......... 204/450–467, 204/600–618; 422/70; 210/656
See application file for complete search history.

(56) References Cited

U.S. PATENT DOCUMENTS

| | | | | |
|---|---|---|---|---|
| 4,417,967 A | * | 11/1983 | Ledley | 204/466 |
| 5,324,401 A | * | 6/1994 | Yeung et al. | 204/452 |
| 5,395,502 A | * | 3/1995 | Pawliszyn | 204/603 |
| 5,503,994 A | * | 4/1996 | Shear et al. | 436/90 |
| 5,582,705 A | | 12/1996 | Yeung et al. | |
| 5,746,901 A | * | 5/1998 | Balch et al. | 204/606 |
| 6,014,213 A | * | 1/2000 | Waterhouse et al. | 356/344 |
| 7,250,098 B2 | | 7/2007 | Inaba et al. | |

* cited by examiner

*Primary Examiner* — Alex Noguerola
(74) *Attorney, Agent, or Firm* — McDermott Will & Emery LLP (57) ABSTRACT

The object of the present invention is that a dynamic range is extended in an electrophoresis unit and concentration differences among a plurality of samples measured simultaneously are increased.
An irradiation time to the samples is adjusted during analysis without changing a sampling time. By shortening the irradiation time, a fluorescence amount of the samples is reduced to cause signal intensity detected by a detector to physically decrease. If the irradiation time is very short (several 100 msec), the irradiation time and fluorescence intensity are in a direct proportional relationship. It is known that, if the irradiation time is reduced to 1/n, the fluorescence intensity, that is, signal intensity to be detected will be 1/n. Thus, for data whose irradiation time is reduced to 1/n during analysis, data obtained by multiplying a substantially measured value by n is used for data analysis as a true value to be originally acquired.

6 Claims, 8 Drawing Sheets

CALCULATE INCLINATION
OF EACH CAPILLARY

FIG.5B

CALCULATE INCLINATION
OF EACH CAPILLARY

FIG.5C

CHECK CALCULATED VALUE
AFTER CHANGING IRRADIATION TIME
OF MEASURED VALUE

ELECTROPHORESIS UNIT AND ELECTROPHORETIC ANALYSIS METHOD

This application claims foreign priority under 35 U.S.C. 119, from Japanese Patent Application No. JP 2006-304686, filed Nov. 10, 2006.

BACKGROUND OF THE INVENTION

1. Field of the Invention

The present invention relates to a technology to separate and analyze nucleic acids, proteins and the like by means of electrophoresis and, for example, relates to a capillary electrophoresis unit.

2. Description of the Related Art

An electrophoresis method using capillaries has been used for the purpose of determining a base sequence and base length of DNA and the like.

The multi-focus method described in U.S. Pat. No. 5,582,705 is known as one of light irradiation methods to a plurality of capillaries. In this method, a capillary on one end of a capillary array consisting of a plurality of capillaries arranged in parallel on a plane substrate or capillaries on both ends of the capillary array are irradiated with a laser light and luminescence generated in the capillary array while the laser light crosses the capillary array by propagating successively from one capillary to the adjacent one is detected by a photodetector. A test sample containing DNA labeled by fluorescence dye is introduced into the capillaries and a laser light is shone in such a way that the laser light propagates through the plurality of capillaries arranged in rows. Laser light shone on the capillaries causes the fluorescence-labeled DNA to generate fluorescence. By measuring fluorescence from each capillary, DNA analysis of the test sample introduced into each capillary can be performed. Proteins and the like can also be analyzed in a similar fashion.

Intensive discussion by the inventors of the application concerned revealed a problem described below.

In order to measure a plurality of samples simultaneously by the method disclosed in U.S. Pat. No. 5,582,705, test sample concentrations must be limited to the dynamic range of an electrophoresis apparatus. Thus, for gene sequencing analysis using electrophoresis, normally time is taken in purifying test samples in a step of electrophoresis pretreatment to prepare approximately uniform test sample concentrations before analyzing such test samples. For example, concentration checks by RNA are done before test samples are set to an electrophoresis apparatus.

However, if the current electrophoresis apparatus is applied to the field of clinical gene function analysis, it is anticipated that samples which do not undergo the adequate pretreatment process will also be measured. For example, it is anticipated that the amount of sample is too small to do concentration checks and thus samples are directly set to an electrophoresis apparatus without doing any concentration check, or samples made to have higher concentrations in advance for expression analysis are analyzed. If, when analyzing a sample whose concentration is not known, the dynamic range of an apparatus is insufficient, a measured signal value may exceed the limits of detection during analysis. In that case, an analyst adjusts the voltage and time when the sample is put in and controls the amount of sample to perform the analysis again.

An object of the present invention relates to suitably analyze a sample even if a concentration thereof is not known.

SUMMARY OF THE INVENTION

The present invention relates to adjustment of time duration in which a sample is irradiated with an excitation light and displaying data calculated from acquired fluorescence intensity, assuming that the fluorescence from the sample is within the measurement range of a detector.

If, for example, a signal value measured by a detector during analysis saturates the measurement range of a detector, the irradiation time to a sample is adjusted without changing the sampling time. By shortening the irradiation time, the amount of fluorescence from the sample is reduced and signal intensity detected by the detector is physically decreased. If the irradiation time is very short (several hundred msec), the irradiation time and fluorescence intensity are in a direct proportional relationship and, if the irradiation time is reduced to 1/n, the fluorescence intensity, that is, signal intensity to be detected will be 1/n. Thus, measured values of data for which the irradiation time is reduced to 1/n during analysis are multiplied by n before being used for data analysis. Then, data points saturated before/after saturation are corrected.

Moreover, for example, in advance before analysis, it is necessary to obtain data showing a relationship between the laser irradiation time and signal intensity values for each capillary. The minimum value of the laser irradiation time required to ensure a substantially analyzable SN ratio can be determined from the relationship between the laser irradiation time and signal intensity values for each capillary. The irradiation time is controlled not to fall below the minimum value to maintain the analyzable SN ratio for each capillary. Signal intensity in each capillary under analysis is sequentially monitored to reflect data values thereof into their correlations before determining the minimum value of the irradiation time. Accordingly, even when simultaneous measurements are made for each capillary (electrophoretic channel) and the laser irradiation time is reduced, a problem such that it is impossible to obtain the fluorescence value of a sample because signal intensity is insufficient for some capillary and the signal is buried in noise, can be avoided.

If, for example, a data binning area is made variable during data acquisition and acquired signal data becomes saturated with respect to a detector, the integrating area is reduced to 1/n. Based on estimation data of signal intensity when the integrating area is reduced to 1/n, signal intensity in the original integrating area can be determined. As preprocessing for analysis, spectral calibration data in accordance with different numbers of cells in the data binning area under conditions of the same sampling time and irradiation time needs to be created.

When, for example, analysis data is processed, generation of pull-up signals (pseudo signals) can be suppressed by using spectral calibration data when the corresponding number of cells in the integrating area is used.

According to the present invention, the dynamic range of the detector can be extended and situations in which a measured signal value becomes saturated with respect to the detection range during analysis and thus re-measurement is necessitated can be avoided.

Also, it becomes possible to measure a plurality of samples simultaneously even if concentrations of each sample vary widely.

DESCRIPTION OF THE PREFERRED EMBODIMENTS

The above and other novel features and advantages of the present invention will be described below with reference to drawings. However, drawings are used exclusively for description and are not intended to limit the scope of the present invention.

First Embodiment

Figure 1:
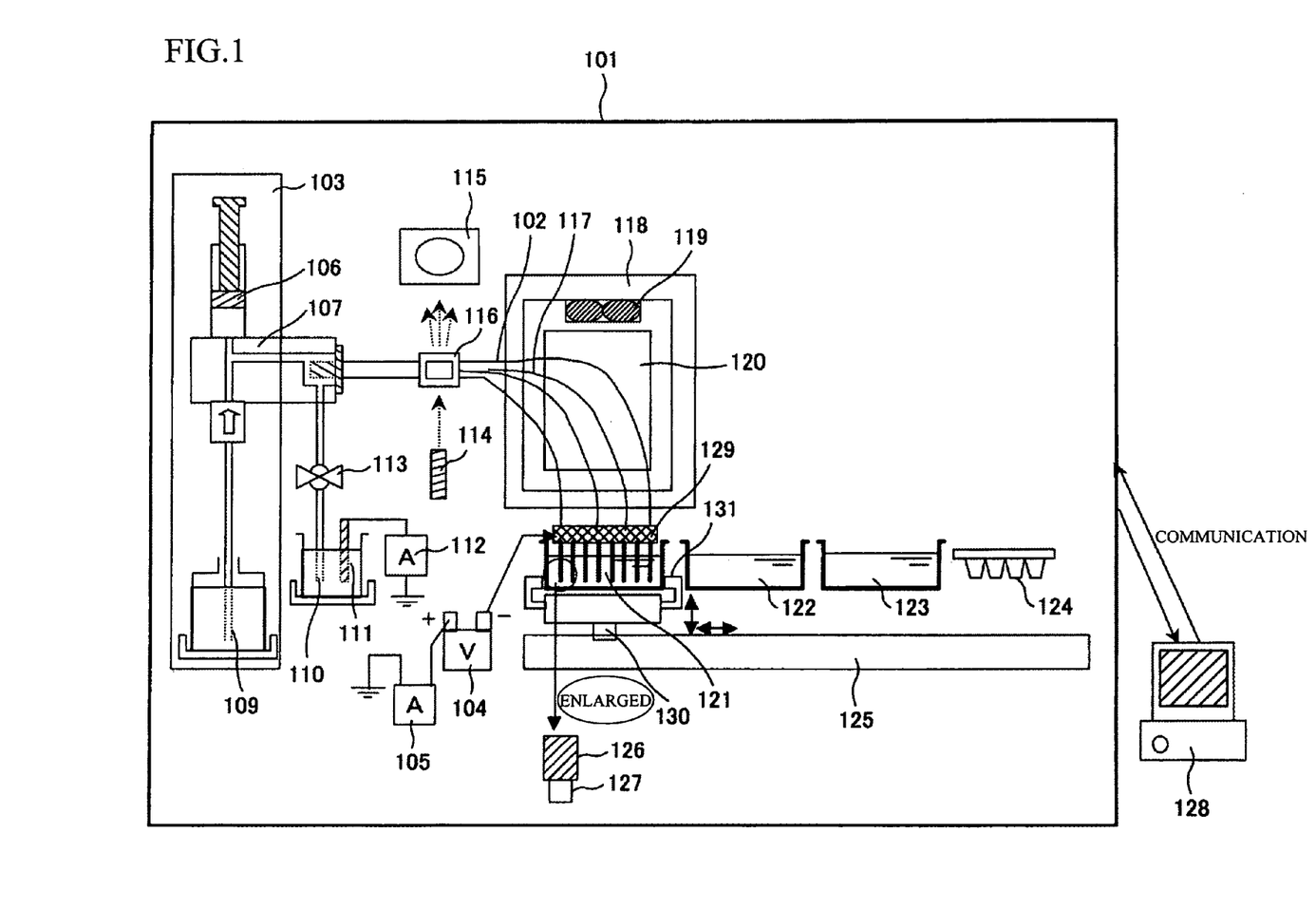
FIG. 1 is a schematic diagram of an electrophoresis unit according to various embodiments.

FIG. 1 is an outline drawing of an electrophoresis unit according to the present embodiment. The configuration of the present apparatus will be described below with reference to FIG. 1.

The present apparatus includes a detection part 116 for optically detecting a sample, a thermostatic oven 118 for maintaining a capillary at a constant temperature, an auto sampler 125 for transporting various containers to a capillary cathode electrode end, a high-voltage power supply 104 for applying a high voltage to the capillary, a first ammeter 105 for detecting a current originating from the high-voltage power supply, a second ammeter 112 for detecting a current flowing to an anode electrode, a capillary array 117 consisting of a single or a plurality of capillaries 102, and a pump mechanism 103 for injecting a polymer into a capillary.

The capillary array 117 is a replacement member including 16 capillaries and includes a load header 129, the detection part 116, and a capillary head. When changing a measuring method, the capillary array is replaced and the length of capillary is adjusted. When any damage or degradation of quality is found in a capillary, the capillary array is replaced by a new one.

A capillary, which is an electrophoresis channel for separating a sample by electrophoresis, is formed of a glass tube whose inside diameter is several tens to several hundreds of μm and outside diameter is several hundreds of μm and the surface thereof is coated with polyimide to improve strength. However, a light irradiation part which is irradiated with laser light has a structure with polyimide coating being removed so that luminescence inside can easily leak out. The inside of the capillary 102 is filled up with a separation medium for providing a migration speed difference during electrophoresis. The separation medium is either fluid or non-fluid and a fluid polymer is used for various embodiments.

The detection part 116 is a member acquiring sample dependent information and, after being irradiated with excitation light, emits light of sample dependent wavelengths. Portions of 16 capillaries near the light irradiation parts are arranged and fixed on an optically flat plane within an accuracy of several μm in height. Two approximately concentric laser lights, which pass through all light irradiation parts successively, are shone from opposite sides of the light irradiation parts during electrophoresis. These laser lights generate information light (fluorescence having a sample dependent wavelength) from a sample, which is emitted outward from the light irradiation parts. The information light is detected by an optical detector 115 to analyze the sample.

Each capillary cathode electrode end 127 is fixed by passing through a hollow metallic electrode 126, with a capillary tip projecting from the hollow electrode 126 by about 0.5 mm. The hollow electrodes, each of which is provided for each capillary, are all integrally mounted on the load header 129. Further, all the hollow electrodes 126 are electrically connected to the high-voltage power supply 104 mounted in a main body and serve as cathode electrodes when it is necessary to apply a voltage in electrophoresis, sample introduction, or the like.

Capillary ends (other ends) opposite to the capillary cathode electrode ends 127 are bundled by a capillary head. The capillary head is a member detached/attached by bundled pressure-resistant airtightness. The capillary head can be connected to a block 107 by pressure-resistant airtightness. Then, a syringe 106 fills in each capillary with a new polymer from the other end. The polymer in the capillary is replaced for each measurement to improve measurement performance.

The pump mechanism 103 includes the syringe 106 and a mechanism to pressurize the syringe. The block 107 is a connection part for allowing the syringe 106, the capillary array 117, an anode buffer container 110, and a polymer container 109 to communicate with one another.

An optical detection part includes an excitation optical system including a light source 114 for irradiating the detection part 116 with laser light (excitation light) and the optical detector 115 for detecting luminescence inside the detection part 116. To detect a sample in a capillary separated by electrophoresis, a light irradiation part of the capillary is shone by the light source 114 and luminescence from the light irradiation part is detected by the optical detector 115.

The thermostatic oven 118 is covered with heat insulating material to maintain the inside of thermostatic oven at a constant temperature and the temperature is controlled by a heating/cooling mechanism 120. Also, a fan 119 circulates and stirs air inside the thermostatic oven to keep the temperature of the capillary array 117 spatially-uniform and constant.

The auto sampler 125 is equipped with three motors and a linear actuator and is movable along three axes, up and down, left and right, and in a depth direction. At least one or more containers can be put on a transport stage 130 of the auto sampler 125. Further, the transport stage 130 is equipped with an electric grip 131, which can hold and release each container. Thus, a buffer container 121, a water container 122, a waste container 123, and a sample container 124 can be transported to the cathode electrode end when necessary. Incidentally, unnecessary containers are stored in a predetermined location in the apparatus.

A main body 101 is used while connected to a control computer 128 via a communication cable. The control computer is equipped with a data viewing area for displaying fluorescence intensity of a sample. An operator can control functions held by the apparatus and receive data detected by the detector in the apparatus, through the control computer 128.

Figure 2A:
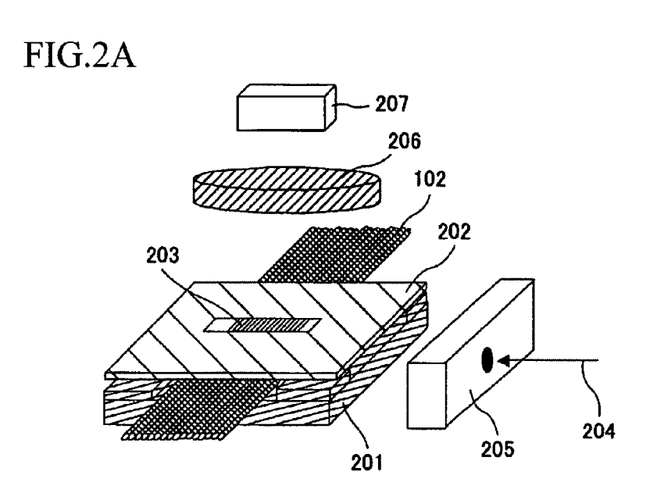
FIG. 2A and FIG. 2B are schematic diagrams of a detection part when a laser light source in a first embodiment of the present invention is used.
Figure 2B:
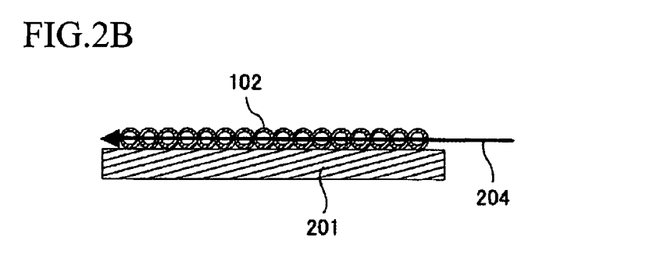

FIG. 2A and FIG. 2B exemplify an optical detection system of the present unit.

In the illustrated example, 16 capillaries 102 are arranged on a capillary holding surface, which is a flat surface of a plane ceramic substrate 201, and fixed by an adhesive or the like to form a capillary array. Each of the capillaries 102 is a quartz glass tube covered with a polyimide thin film, but the film is removed in a laser irradiation part 203, exposing the quartz. The inside diameter/outside diameter of the quartz tube are 50/323 µm and the outside diameter of the capillary including the polyimide thin film is 363 µm, FIG. 2B shows a schematic diagram of a cross section obtained by cutting a portion of the detection part along a plane perpendicular to the capillary. There are 16 capillaries 102, and laser light 204 first shines on the outermost capillary 102 and, after passing through it, shines on the next capillary 102. The laser light 204 passes through a plurality of capillaries one by one in this way before coming out of the outermost capillary on the opposite side. Since the capillary has a cylindrical shape and a polymer is filled therein, the capillary provides a light focusing function like a convex lens. Divergence of the laser light 204 is thereby suppressed. By shining the laser light 204 from both the left and right sides, the laser light 204 of uniform intensity can be shone on approximately all capillaries. Thus, 16 samples can simultaneously be detected while maintaining high sensitivity.

A laser usually continues to output during analysis and the irradiation time for samples inside the capillaries is controlled by a shutter 205. The irradiation time for the capillaries 102 is controlled by synchronizing opening/closing of the shutter 205 with timing of data acquisition by an optical detector 207. Also, acquired signal values of the optical detector 207 are controlled not to become saturated.

Figure 3:
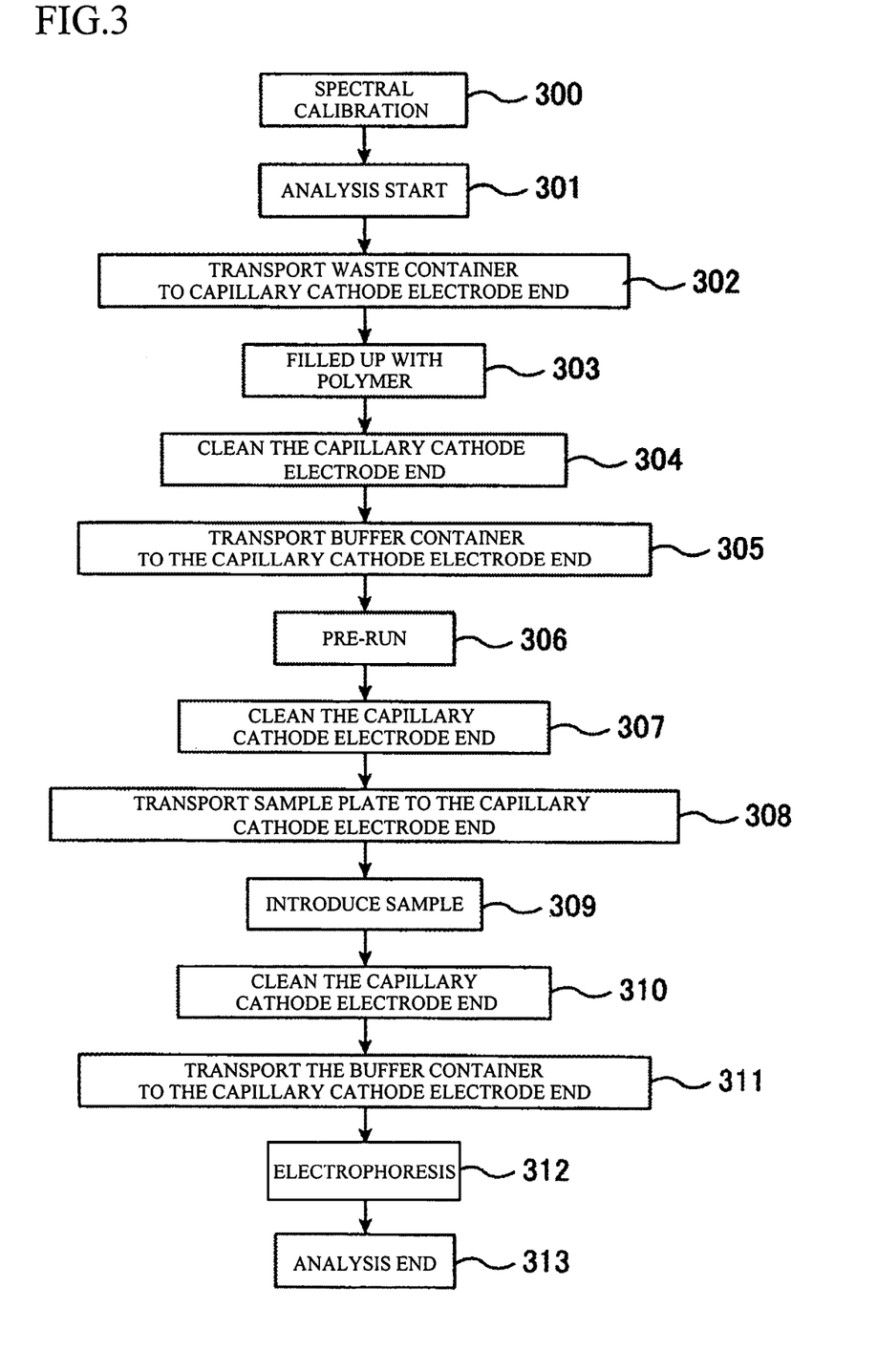
FIG. 3 is a flow diagram showing a flow from an analysis start to an analysis end.

A basic procedure for electrophoretic analysis will be described below mainly with reference to FIG. 3. Before analyzing any sample by performing electrophoresis, spectral calibration is performed for each replacement of capillary. In the spectral calibration, reference spectral data is obtained from migration of a known DNA sample calibrated from a group of pigments to be analyzed, for example, four fluorescence dye. (300) This is always done after replacing the capillary array 117 when degradation of the capillary 102 is anticipated or the length of the capillary 102 is changed depending on analysis.

The basic procedure for electrophoretic analysis can roughly be divided into preparations, filling of polymer (303), pre-run (306), sample introduction (309), and migration analysis (312).

First, preparations before starting electrophoresis will be described. An operator sets the following things to the apparatus before starting measurement: the buffer container 121 containing a buffer solution, the water container 122 containing pure water for washing capillaries, the waste container 123 for discharging polymers in the capillaries, the polymer container 109 containing a polymer as a separation medium, and the sample container 124 containing samples to be measured.

The anode buffer container 110 is sufficiently filled with a buffer solution so that both an electrode (GND) 111 and a communicating tube are soaked in the buffer solution. The buffer solution is, for example, an electrolytic solution for electrophoresis commercially available from various manufacturers.

A sample to be analyzed is dispensed into a well of the sample container 124. The sample is, for example, a PCR product of DNA.

A washing solution for washing the capillary cathode electrode end 127 is dispensed into the water container 122. The washing solution is, for example, pure water.

A separation medium for electrophoresis of samples is poured into the syringe 106. The separation medium is, for example, polyacrylamide-based separation gel for electrophoresis commercially available from various manufacturers (hereinafter referred to as a polymer).

The buffer container 121 is sufficiently filled with a buffer solution so that both the hollow electrode 126 and capillary cathode electrode end 127 are soaked in the buffer solution. If measurement is started when the amount of buffer solution is insufficient or the buffer container is empty, a discharge may occur between the high-voltage cathode and something else with a low potential when a high voltage is applied. Further, buffer levels of both are preferably equal. This is intended not to allow polymers in the capillaries to move due to pressure resulting from a difference in height.

All channels used for electrophoresis and those used for transporting a polymer to such channels must be filled with polymer before starting measurement. When the apparatus is used successively, the channels are usually filled with polymer.

When content of a channel is replaced by polymer after replacing the capillary array or washing the channel, an operator operates the pump mechanism in the apparatus or manually operates the syringe to replace the channel content with polymer. Subsequently, the operator visually checks for any residual bubbles or mixing of foreign matter in the channel. Then, after completing the preparations, the operator operates the present apparatus to start an analysis. The analysis here is, for example, an analysis involving application of a high voltage to electrophoresis channels.

The present apparatus starts an analysis in accordance with instructions from the control computer 128 (301). In preparation for polymer injection into the capillaries, the apparatus first transports the waste container to the capillary cathode electrode end using a auto sampler mounted on the apparatus (302). Subsequently, polymers are injected into the capillaries using the pump mechanism provided with the apparatus (303). When a predetermined amount of polymer is injected, the auto sampler transports the water container to the capillary cathode electrode end. The capillary cathode electrode end is washed by soaking it in pure water inside the water container (304). Next, the auto sampler transports the buffer container to the capillary cathode electrode end (305).

A predetermined voltage is applied to start pre-run (306). The pre-run is intended, prior to a primary analysis step in which a sample is introduced and electrophoresis is performed, to analyze a polymer state in the capillary to make the polymer state fit for analysis. In the pre-run, a voltage of about several kV to several tens of kV is usually applied for several minutes to several 10 minutes. When the pre-run ends, the capillary cathode tip is washed again using the water container (307) and the sample container 124 is transported to the capillary cathode electrode end (308). Then, when a voltage of about several kV is applied to the capillary cathode electrode in a sample solution contained in the sample container 124, an electric field is generated between the sample solution and the anode electrode. A sample in the sample solution is introduced into the capillary by this electric field (309). When the sample introduction ends, the capillary cathode electrode end is washed using the water container (310) and the buffer container is again transported to the capillary cathode electrode end (311). Subsequently, electrophoresis is started by applying a predetermined voltage (312).

The electrophoresis (312) means that by providing mobility to a sample for the capillary by action of the electric field generated between the cathode and anode buffer solution, the sample is separated based on a difference of mobility depending on sample properties. Those portions of the separated sample that reach the detection part first are optically detected first. If the sample is DNA, for example, differences in mobility arise due to the base length. Therefore, DNAs, which have short base length and therefore, high traveling velocity, pass first through the detection part. Since DNA has a fluorescent substance attached to itself in advance, such DNA can optically be detected by the detection part. The measuring time and voltage application time are usually set by fitting to the sample having the longest electrophoretic time.

When a predetermined time has passed after starting to apply a voltage and planned data has been acquired, application of the voltage is stopped to end electrophoresis (313). The above is a sequence of a series of measurements.

Performance obtained from the present embodiment will be described below.

Figure 4A:
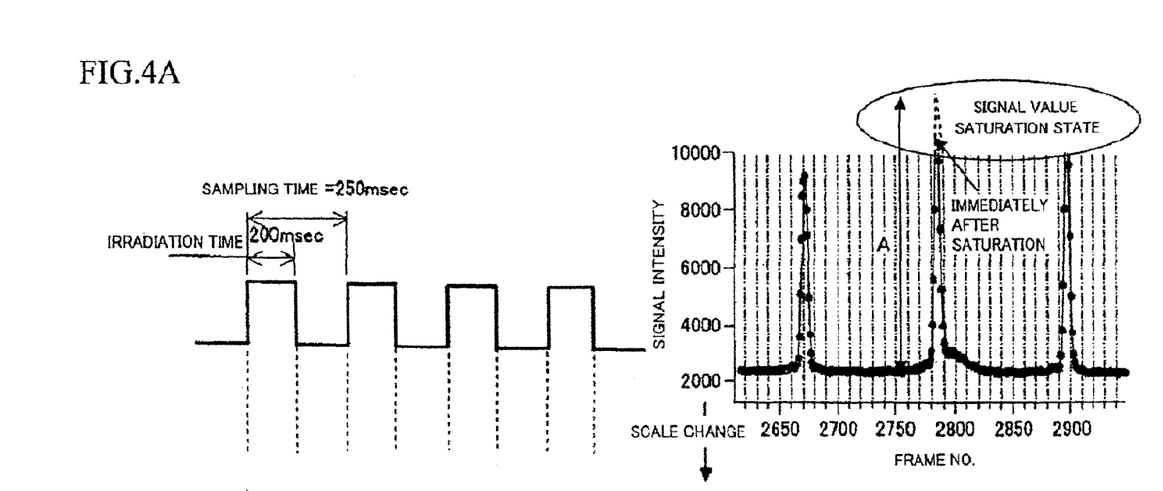
FIG. 4A and FIG. 4B are schematic diagrams showing an irradiation time to samples according to a first embodiment of the present invention and detected signal values.
Figure 4B:
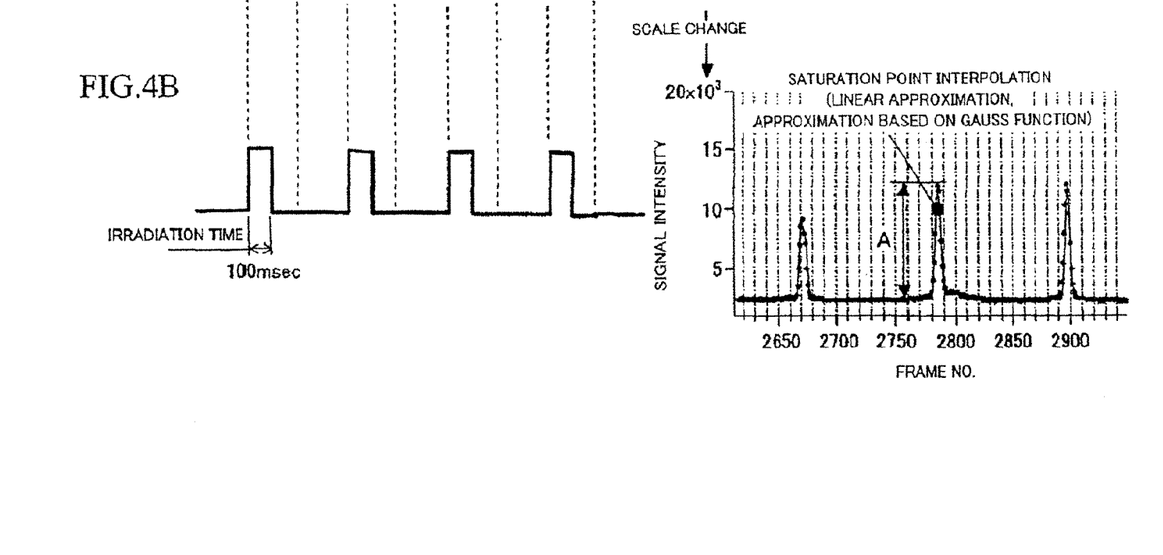

FIG. 4A and FIG. 4B show the sampling time and laser irradiation time during analysis. Signal intensity values acquired by a detector in that case are also shown. In FIG. 4A, the sampling time is set to 250 msec and the irradiation time is set to 200 msec. Thus, while the correct value could be detected for the first DNA fragment because signal intensity was below the saturation limit value of the detector, no correct value could be detected for the second and subsequent fragments because signal values become saturated. The data detection and display range here is 10000 or below. Thus, when data just after saturation is acquired or acquired data becomes saturated, as shown in FIG. 4B, the irradiation time is changed to 100 msec for the next sampling. The sampling time of 250 msec remains unchanged.

Here, when the irradiation time is very short (several 100 msec), the irradiation time and fluorescence intensity are in a direct proportional relationship. It is known that, if the irradiation time is reduced to $1/n$, the fluorescence intensity, that is, signal intensity to be detected will be $1/n$.

Since the irradiation time is halved from 200 msec to 100 msec, an actual signal value A obtained for the irradiation time 200 msec will be detected as A/2. Thus, A is displayed on the data viewing area after multiplying the actually detected A/2 by 2. The data viewing area can scale up to 20000 for detection and display, which is twice the original size, and thus the substantially detectable signal intensity range can be extended.

Simultaneous measurement is made for each capillary in the present system and thus, if the laser irradiation time is shortened, the fluorescence value of a sample may not be obtainable because signal intensity is insufficient for some capillary and the signal is buried in noise. Therefore, it is necessary to obtain data showing a relationship between the laser irradiation time and signal intensity values for each capillary in advance before analysis.

Here when saturated, data can be obtained from data just after saturation and that just before saturation by linear approximation or by approximation using the Gauss function. When actual fluorescence intensity could not be measured due to saturation during sampling, data can be obtained by interpolating data before/after saturation, using an approximate function.

Figure 5A:
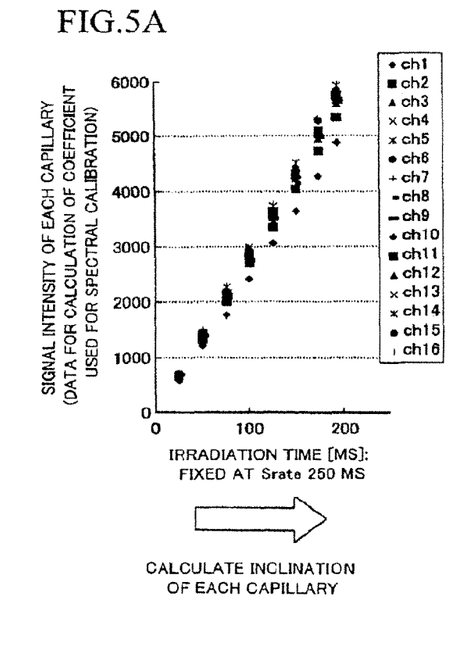
FIG. 5A, FIG. 5B and FIG. 5C are schematic diagrams showing the irradiation time and signal intensity in each capillary according to the first embodiment of the present invention.
Figure 5B:
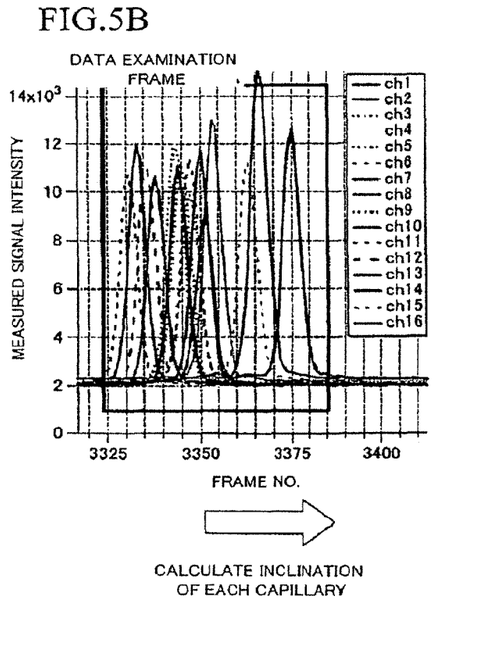
Figure 5C:
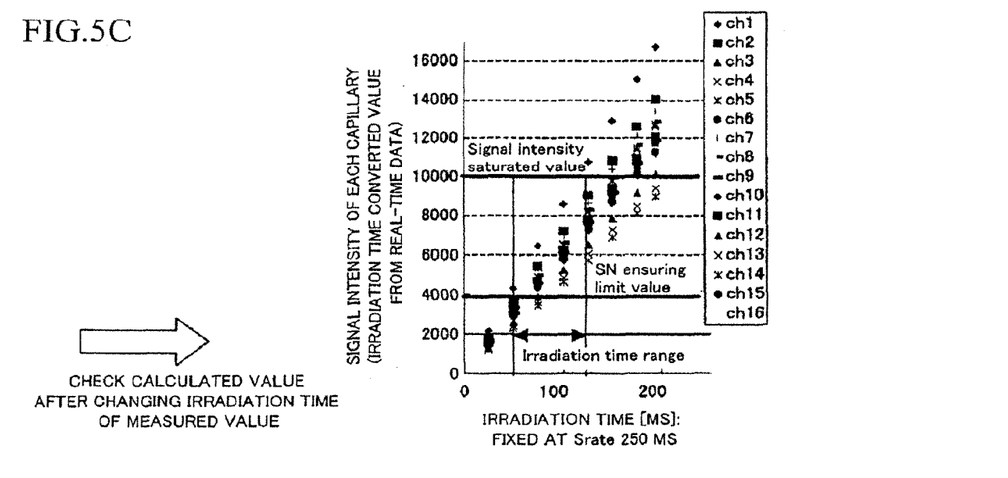

FIG. 5A shows the ratio of the irradiation time and signal intensity for each capillary. This data is obtained by measuring signal intensity of each capillary by changing the laser irradiation time when spectral calibration data before analysis processing is obtained. The data can be recorded in a control computer. The minimum value of the laser irradiation time required to ensure a substantially analyzable SN ratio can be estimated from the relationship between the laser irradiation time and signal intensity values for each capillary. FIG. 5B shows acquired signal intensity data of each capillary during analysis in real time. While signal intensity of each capillary being sequentially monitored in a certain extent of frame range, as shown in FIG. 5B, the excitation light irradiation time and the signal intensity value that is to be acquired are calculated, as shown in FIG. 5C. Since the minimum signal intensity has been calculated from the upper limit value of data area that can be acquired by a detector and the limit value of SN ratio required to ensure analysis precision, an excitation light irradiation time in a range thereof is set.

Thanks to a function thereof, an analyzable SN ratio is maintained in every capillary, seemingly extending the dynamic range of the apparatus.

Second Embodiment

A second embodiment will be described below.

Figure 6A:
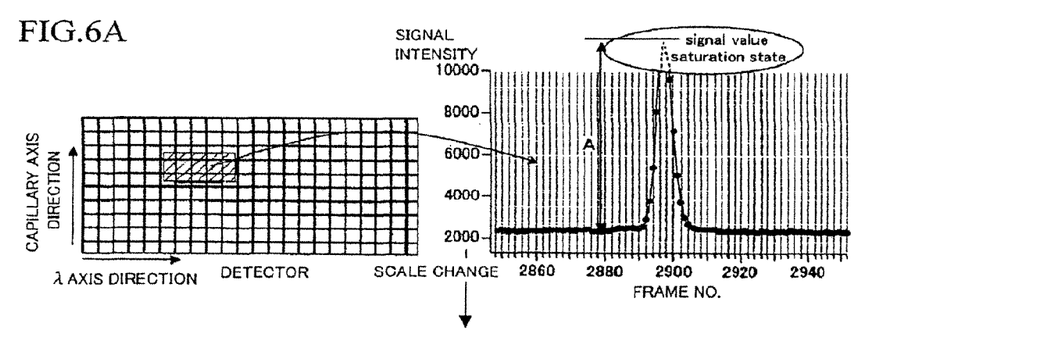
FIG. 6A, FIG. 6B and FIG. 6C are schematic diagrams illustrating dynamic range extension due to a change of a data acquisition area for a detector in a second embodiment of the present invention.
Figure 6B:
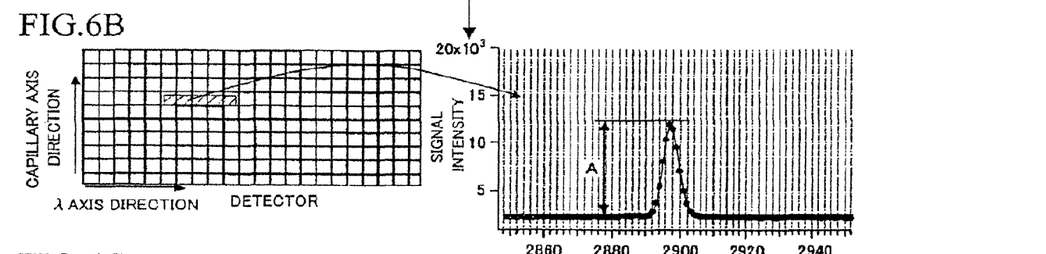
Figure 6C:
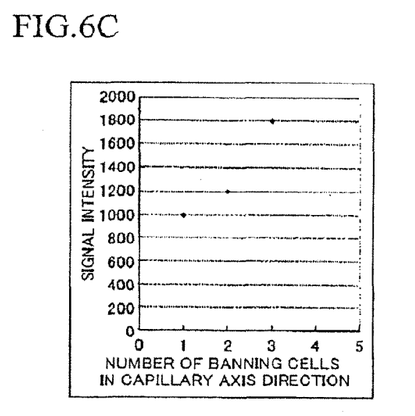

In the second embodiment, reduction in acquired signal intensity by a method of controlling a data binning area of a detector, instead of the excitation light irradiation time to a sample, will be described. In FIG. 6A, acquired data is saturated when the number of data integrating cells in the capillary space direction is 3. Thus, as shown in FIG. 6B, if the number of data integrating cells in the capillary space direction is 1 with the same sampling time and excitation light irradiation time, the number of cells to be integrated will be ⅓ and thus, acquired signal intensity by a detector will be smaller to fall below the limit value of detection so that correct data can be obtained. In this case, as shown in FIG. 6C, like the first embodiment, signal intensity values when the number of cells is changed need to be measured in each capillary when spectral calibration data is obtained. Based on this relationship, the reduced value of signal intensity when the number of cells is reduced from 3 to 1 can be determined. That is, a correlation between the number of cells and signal intensity is derived and, by multiplying substantially measured data by n, intrinsic signal intensity can be calculated.

Figure 7A:
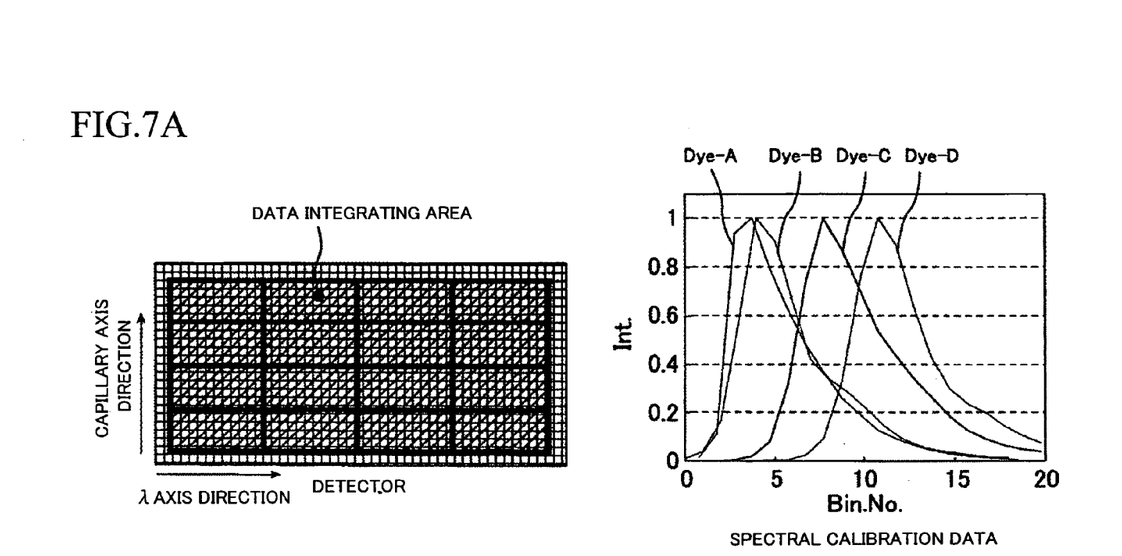
FIG. 7A and FIG. 7B are schematic diagrams showing spectral calibration data according to the second embodiment of the present invention.
Figure 7B:
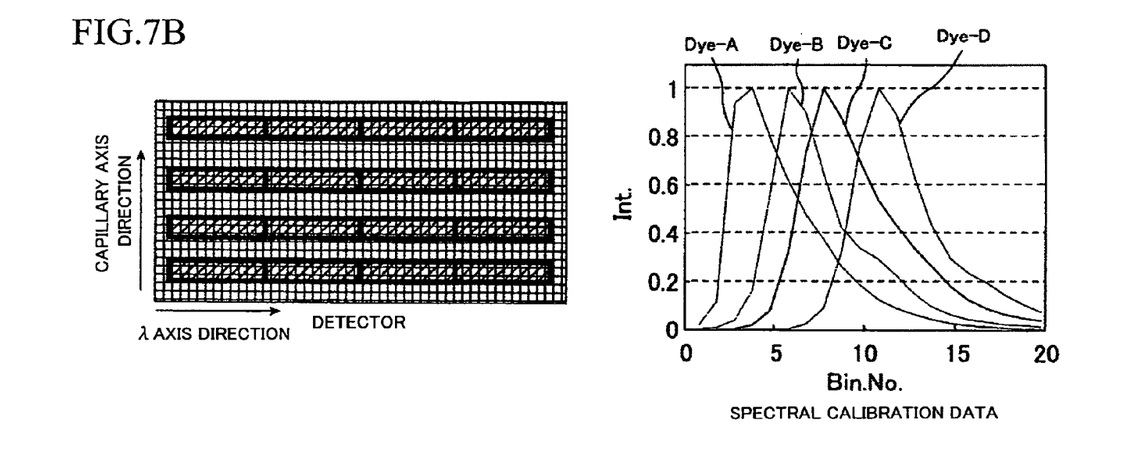
Figure 8:
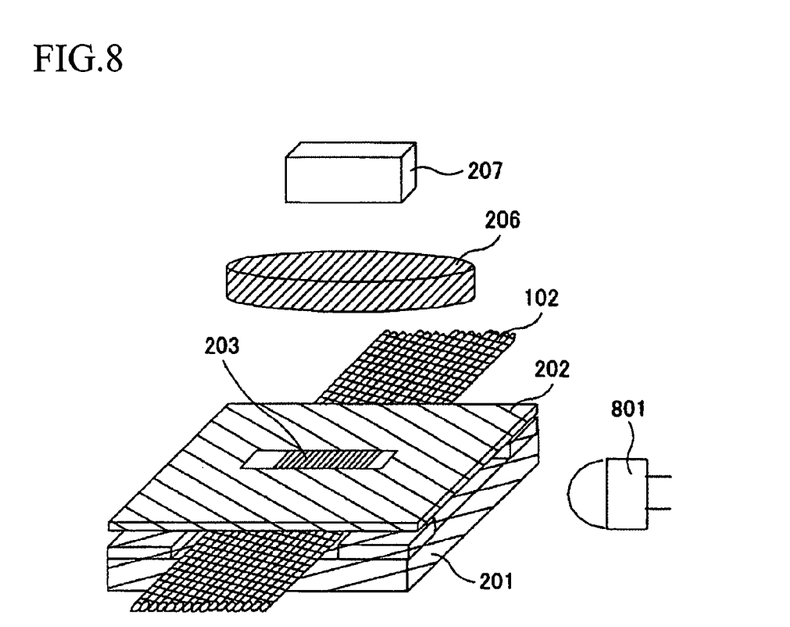
FIG. 8 is a schematic diagram of when an LED light source in a third embodiment of the present invention is used.

FIG. 7A and FIG. 7B show spectral calibration data in analysis processing when the sampling time and irradiation time are fixed and the data binning area is changed. As preprocessing for analysis, spectral calibration data in accordance with different numbers of cells in the data binning area under conditions of the same sampling time and irradiation time needs to be created.

When the data binning area in FIG. 7A has, for example, 3×14 cells per integrating area and the data binning area in FIG. 7B has, for example, 1×14 cells per integrating area, signal intensity can be made greater in (a). In actual analysis, (a) is usually used, but when acquired signal data is saturated, the data binning area is switched to (b) and spectral calibration data also uses (b).

When analysis data is processed, generation of pull-up signals (pseudo signals) can be suppressed by using spectral calibration data when the corresponding number of cells in the integrating area is used.

Third Embodiment

A third embodiment will be described below.

While a laser is used as a light source in the first embodiment to adjust the irradiation time of excitation light by a shutter, a case in which an LED is used as an excitation light source and the LED is caused to blink at high speed will be described in the present embodiment with reference to FIG. 7A and FIG. 7B. Because an LED light source 701 has a fast response time of several μsec to ON/OFF switching, the shutter is not necessary when the excitation time is controlled by ON/OFF. By driving ON/OFF of the LED light source 701 in synchronization with timing of data acquisition of the optical detector 207, it becomes possible to adjust the irradiation time to samples and to prevent saturation of acquired signal values.

Fourth Embodiment

A fourth embodiment will be described below.

In the present embodiment, a control device has a function to predict that the next data will be saturated based on an inclination of a graph of the detection time/signal intensity, to automatically change the excitation time and viewing scale, when data currently being acquired approaches a saturation state on a detector.

Embodiments of the present invention have been described, but the present invention is not limited to these embodiments and those skilled in the art can understand that various modifications can be made within the scope of the invention defined by the appended claims. Suitable combinations of each embodiment are also included in the scope of the present invention.

What is claimed is:

1. An electrophoresis unit having a plurality of electrophoretic channels, an excitation optical system for irradiating a sample separated by electrophoresis on said electrophoretic channels with an excitation light, a detector for detecting fluorescence emitted from said sample, and a data viewing area for displaying fluorescence intensity of said sample, wherein:
    a data binning area of said detector is controlled during electrophoretic analysis, and
    a viewing scale of the fluorescence intensity changes on the data viewing area to avoid a saturation state when the fluorescence intensity is saturated or before the fluorescence intensity is saturated.

2. The electrophoresis unit according to claim 1, further comprising an LED light source for emitting the excitation light.

3. The electrophoresis unit according to claim 1, wherein a limit range (maximum analysis value-minimum analysis value) of the fluorescence intensity can be displayed by recording the fluorescence intensity for each electrophoretic channel.

4. The electrophoresis unit according to claim 1, wherein spectral calibration data processing is performed for a plurality of data binning areas when spectral calibration data is created.

5. The electrophoresis unit according to claim 1, wherein sampling data for which actual fluorescence intensity could not be measured due to saturation is interpolated by using an approximate function based on data before/after the saturation.

6. An electrophoretic analysis method comprising:
    preparing a plurality of electrophoretic channels;
    separating a sample by electrophoresis on the electrophoretic channels;
    irradiating the sample separated by electrophoresis with an excitation light by means of an excitation optical system;
    detecting fluorescence emitted from the sample by a detector; and
    displaying fluorescence intensity of the sample on a data viewing area, wherein:
    a data binning area of said detector is controlled, and
    a viewing scale of the fluorescence intensity changes on the data viewing area to avoid a saturation state when the fluorescence intensity is saturated or before the fluorescence intensity is saturated.

* * * * *